United States Patent [19]
Quinn et al.

[11] Patent Number: 5,152,756
[45] Date of Patent: Oct. 6, 1992

[54] DISTAL GRIPPING TIP FOR ENTERAL FEEDING TUBE

[75] Inventors: David G. Quinn, Grayslake; Erik Andersen, Vernon Hills, both of Ill.

[73] Assignee: Corpak, Inc., Wheeling, Ill.

[21] Appl. No.: 660,536

[22] Filed: Feb. 25, 1991

Related U.S. Application Data

[63] Continuation-in-part of Ser. No. 469,218, Jan. 24, 1990, Pat. No. 5,037,387.

[51] Int. Cl.⁵ .............................................. A61M 31/00
[52] U.S. Cl. ..................................... 604/270; 604/280
[58] Field of Search ................... 604/51, 93, 264, 266, 604/267, 270, 280; 128/772, 658

[56] References Cited

U.S. PATENT DOCUMENTS

| | | | |
|---|---|---|---|
| 1,736,182 | 11/1929 | Wilkins | 604/270 |
| 3,189,031 | 6/1965 | Andersen | 604/270 |
| 4,594,074 | 6/1986 | Andersen et al. | 604/270 |
| 4,613,323 | 9/1986 | Norton et al. | 604/270 X |
| 4,643,194 | 2/1987 | Fogarty | 128/668 |
| 4,659,328 | 4/1987 | Potter et al. | 604/170 |
| 4,692,152 | 9/1987 | Emde | 604/164 |
| 4,778,455 | 10/1988 | Kousai et al. | 604/270 |
| 4,846,193 | 7/1989 | Tremulis et al. | 128/772 |
| 4,854,330 | 8/1989 | Evans, III et al. | 128/772 |
| 5,057,091 | 10/1991 | Andersen | 604/270 |

FOREIGN PATENT DOCUMENTS

| | | | |
|---|---|---|---|
| 0042703 | 12/1981 | European Pat. Off. | |
| 0591963 | 7/1925 | France | 604/270 |
| 1306586 | 4/1987 | U.S.S.R. | 604/270 |

Primary Examiner—John D. Yasko
Assistant Examiner—Adam J. Cermak
Attorney, Agent, or Firm—Wallenstein, Wagner & Hattis, Ltd.

[57] ABSTRACT

An improved enteral feeding tube (10) having a distal (12) and a proximal end (14). The tube (10) has a generally circular cross-section, and includes an attachment (22) or extension of the tube made of flexible polyurethane that is adhered to the distal end (12) of the enteral feeding tube (10). The attachment (22) comprises a generally rigid stem portion (24) extending from the distal end (12) of the enteral tube (10), and along an axis generally parallel to the axis of the feeding tube. The attachment (22) further comprises a spherical tip (28) at one end of the rigid stem portion (24).

16 Claims, 1 Drawing Sheet

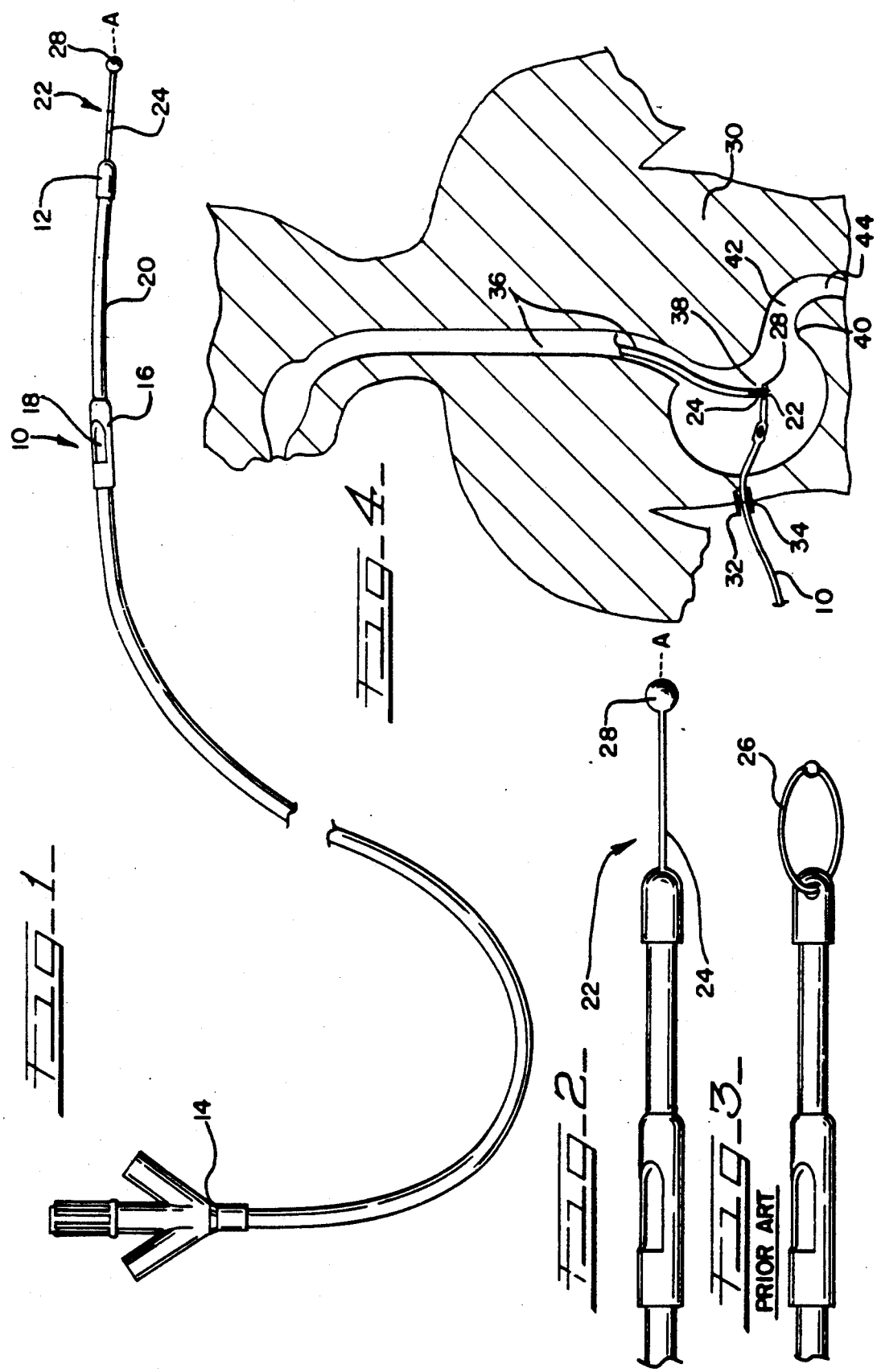

DISTAL GRIPPING TIP FOR ENTERAL FEEDING TUBE

RELATED APPLICATION

This is a continuation-in-part application of U.S. application Ser. No. 07/469,218, filed Jan. 24, 1990 now U.S. Pat. No. 5,037,387, entitled Distal Gripping Tip for Enteric Feeding Tube.

DESCRIPTION

1. Technical Field

The invention relates to the field of catheters, and especially those used in enteral feeding. More particularly, the invention relates to improvements in enteric or enteral feeding tubes, and to their improved placement within the body of a patient.

2. Background of the Invention

Enteral feeding tubes are well-known in the art. One such enteral feeding tube is disclosed, for example, in U.S. Pat. No. 4,594,074, issued to Andersen et al. on Jun. 10, 1986, and assigned to the predecessor of the assignee of the present invention.

Percutaneous access through a surgically formed gastrostomy permits direct placement of an enteral feeding tube within the stomach. The feeding tube may be inserted through a conventional tube in an ostomy, for example, a percutaneous endoscopic gastrostomy (PEG) tube. Correct placement of an enteral feeding tube within the stomach or small intestine is currently facilitated by an attachment adhered to the distal end of the enteral feeding tube. This enteral feeding tube attachment includes a small hole through which a suture is looped.

After the enteral feeding tube has been placed through the ostomy and into the stomach, the loop of this suture aids in proper positioning of the distal end of the feeding tube within portions of the gastrointestinal tract beyond the pylorus valve. Particularly, the loop is grasped by endoscopic forceps. By manipulation of the forceps, the loop and the distal end of the enteral feeding tube are properly positioned within either the duodenum or the jejunum.

There are, however, certain drawbacks to this prior art, loop-containing attachment. First, the suture is intended to lead and extend in a forward direction from the distal end of the enteral feeding tube. The suture is, however, made of a non-rigid fabric. For this reason, as the enteral feeding tube is inserted through the PEG tube or cannula within the ostomy, the suture has a tendency to trail the feeding tube. This tendency causes the suture to become reversed, and to "double-over" the sides of the feeding tube. The suture thus becomes lodged between the enteral feeding tube and the PEG tube. As a result, the effective outer diameter of the feeding tube is increased. Because the actual outer diameter of the enteral feeding tube is designed to be only slightly smaller than the inner diameter of the PEG tube, this "doubling-over" of the suture inhibits the free movement of the enteral feeding tube through the PEG tube.

Yet another problem arises when the feeding tube has been inserted within the body of the patient. As discussed above, the loop of the suture is grasped by a pair of endoscopic forceps. As it is moved through the body, the suture loop absorbs and tends to become wetted by various body fluids. When the enteral feeding tube is properly positioned within the duodenum or jejunum and the endoscopic forceps are opened to release the wetted suture, that suture may nevertheless stick to the forceps. As a result, the suture and the enteral feeding tube to which it is attached may follow the forceps while the forceps are being withdrawn from the body cavities. In this manner, the enteral feeding tube may be moved from its intended position.

As a result of these shortcomings of the prior art, it was deemed desirable to design a modified attachment for enabling precise placement of an enteral feeding tube within a body cavity.

An object of the present invention is an improvement in an enteral feeding tube which facilitates entry of that tube through yet another tube in an ostomy, such as a cannula or a PEG tube. Another object of the invention is an improvement in an enteral feeding tube which ensures proper placement of that tube within the body. Still another object of the present invention is an attachment for an enteral feeding tube which maintains a relatively low risk of puncturing organs as that tube is moved through the body.

SUMMARY OF THE INVENTION

The invention is an improved enteral feeding tube with a unique distal end extension which may be integrally molded with an enteral feeding tube or be initially a separate attachment secured around the end of a conventional enteral feeding tube. This improved extension or attachment results in important advantages to be described. The tube is of the type generally known in the prior art, and may have a conventional, generally circular cross-section. The attachment comprises a generally semi-rigid stem portion. By "rigid" is meant that the stem maintains a normally straight rigid configuration pointed upwardly, but can be flexed somewhat to permit its manipulation within the patient's body in a manner to be described. This stem portion most advantageously has a diameter or thickness less than that of the adjacent distal end portion of the enteral feeding tube so that there is an abutment or shoulder formed between this stem portion of the adjacent portion of the enteral feeding tube. The stem portion projects from this adjacent portion of the enteral feeding tube along an axis generally parallel to the axis of that tube. An enlarged tip, preferably a spherical tip, is formed at one end of the rigid stem portion. This enlarged tip forms an abutment shoulder between the tip and stem portion. The length of the stem portion should be sufficient to permit a conventional forceps to grip the stem portion only. To this end, the length of the stem portion should be in excess of the thickness of said tip, or have a length at least several times its thickness. While not necessary, in accordance with the broader aspects of the invention, it is most advantageous that the enteral feeding tube passageway terminates adjacent the distal end of the enteral feeding tube in a lateral discharge opening in advance of the stem portion. In such case, the stem portion can be conveniently and effectively grasped by the forceps without occluding this lateral discharge opening.

In a preferred embodiment of the enteral feeding tube of the present invention, the attachment is made of a flexible polyurethane. As indicated above, the attachment may be either adhered to or integrally molded with the distal end of the feeding tube.

BRIEF DESCRIPTION OF THE DRAWINGS

FIG. 1 is perspective view of the improved enteral feeding tube in accordance with the invention, and including the attachment of the invention as secured to that feeding tube;

FIG. 2 is a perspective view of the attachment shown in FIG. 1;

FIG. 3 is a perspective view of the distal end of an enteral feeding tube in accordance with the prior art, and showing the looped suture used in such prior art devices; and FIG. 4 is an illustrative diagram showing the placement and insertion of the present invention for gripping and movement by a pair of endoscopic forceps.

DETAILED DESCRIPTION OF THE PREFERRED EMBODIMENT

Referring now to the drawings, one aspect of the present invention is shown in FIG. 1, and another aspect is illustrated in FIG. 2. While the inventions in these preferred embodiments are described in connection with an enteral feeding tube, these embodiments are described by way of example only. The principles of the present invention may be applied to all types of catheter tubes.

In the first aspect, the invention comprises an improved enteral feeding tube 10. The tube 10 shown in this embodiment has a distal 12 and a proximal end 14, and has a generally circular cross-section. In other respects, this tube 10 is similar to that described in U.S. Pat. No. 4,594,074, issued to Andersen et al. on Jun. 10, 1986. Thus, it includes a bolus 16 adjacent to the distal end 12. This bolus 16 includes an opening 18 having a generally ellipsoidal edge configuration and defining a tube outlet. The tube 10 includes a weighted end section 20 between the bolus 16 and the distal end 12. This weighted end section 20 is weighted with metal discs or any other weighing means conventional in the art.

The enteral feeding tube 10 of the present invention includes an attachment 22 which replaces an attachment used in prior art enteral tubes. This attachment 22 is shown secured to an enteral tube in FIG. 1, and is also shown alone in FIG. 2.

For reasons that will become apparent, the attachment 22 should be both somewhat rigid and yet flexible. Particularly, the attachment 22 should be sufficiently rigid so that its stem portion 24 will remain upright when the attachment is pointed upwardly. The attachment 22 should be sufficiently flexible so as to not harm tissue when moved within the body of a patient, and sufficiently flexible so that forceps may bend that stem portion 24. Thus, an ideal and preferred material for the attachment 22 is polyurethane which is the same material as that preferred for enteral feeding tubes of the prior art.

Because this stem portion 24 is made of a rigid material like polyurethane, it avoids the tendency of prior art sutures 26 (FIG. 3) to become reversed or "doubledover" the sides of the feeding tube as that tube is inserted through yet another tube, such as a PEG tube or cannula, extending from an ostomy. Polyurethane also has sufficient flexibility so that the endoscopist may grasp the stem portion 24 with the endoscopic forceps and twist or bend it as desired as the enteral feeding tube 10 is moved from the stomach and into the duodenum or jejunum.

The attachment 22 has an enlarged socket-forming portion 2 from which axially extends the stem portion 24 extending generally parallel to the axis of the enteral feeding tube 10. The socket-forming portion 25 of the attachment may be secured around the distal end 12 of the enteral feeding tube 10 with tetrahydrofurane (THF). Particularly, the distal end 12 of the enteral feeding tube 10 is wetted by dipping into either pure THF or a solution of 93% THF and 7% polyurethane. Adhesion takes place rapidly after the socket-forming portion 25 of attachment 22 is slipped over the wetted portion of the tube 10.

Although the above-described embodiment contemplates a discrete and separate attachment 22 which is secured by tetrahydrofurane to the enteral feeding tube 10, it will be understood by those skilled in the art that the attachment 22 may instead be integrally molded, i.e., as one piece, together with the tube 10.

As previously indicated, the stem portion most advantageously has a diameter or thickness less than that of the adjacent distal end portion of the enteral feeding tube, so that there is an abutment or shoulder formed between this stem portion of the adjacent portion of the enteral feeding tube. The length of the stem portion 24 should be sufficient to permit a conventional forceps to grip the stem portions only. To this end, the length of the stem portion should have a length at least several times its thickness.

In the present preferred embodiment, this stem portion 24 has a circular crosssection, a diameter of about one (1) millimeter, and a length of approximately eighteen (18) millimeters. The stem portion 24 extends from the distal end 12 of the enteral feeding tube 10 which typically may have a diameter of from 1.5 mm to 3 mm millimeters, and along an axis A that is generally parallel to the axis of a straightened, extended feeding tube 10.

The attachment 22 also comprises a generally enlarged tip, preferably a spherical tip 28. This enlarged tip forms an abutment shoulder between the tip and stem portion. In this embodiment, this tip is integrally molded to one end of the rigid stem portion 24. The tip 28 is made generally spherical to lessen the danger that the attachment 22, and particularly its stem portion 24, punctures the tissue when the improved tube 10 with its leading attachment 22 is moved through the gastrointestinal tract.

The length of the stem portion 24 preferably is greater than the diameter or maximum thickness of the tip. The tip 28 preferably has a character of about (4) millimeters when the stem portion has a diameter of about 1 millimeter. However, it will be understood by those skilled in the art that any shape which has the effect of distributing force over an enlarged area will be generally suitable for use as a tip 28. More particularly, any edgeless shape will be suitable for use as a tip in accordance with the broadest aspect of the present invention.

Referring now to FIG. 4, the improved enteral feeding tube 10 of the present invention is shown in place within a patient 30. The enteral feeding tube 10 is shown passing through a cannula 32 in the ostomy or stoma 34. However, a PEG tube or any other comparable device which parts the tissue of the stoma 34 may be used in lieu of the cannula 32. It is also contemplated that a sufficiently narrow enteral feeding tube in accordance with this invention could be placed into the stomach through an endoscope.

Also shown in FIG. 4 are an endoscope 36 positioned in the stomach of the patient 30. Through the use of the endoscope 36, the endoscopist may view the attachment 22, including the stem portion 24 and its tip 28. Endoscopic forceps 38 are positioned in the stomach through the endoscope 36, and the endoscopist grips the stem portion 24 of the attachment 22 with the forceps 38. The endoscopist may now move the attachment 22 and the tube 10 through the pylorus valve 40 of the stomach and into position in the duodenum 42 or the jejunum 44. The endoscopist is free to twist the flexible stem portion 24 to facilitate this positioning. In addition to its role in lowering the chances of puncturing the intestine while the tube 10 is moved into position, the tip 28 also prevents the forceps from slipping off of the leading end of the stem portion 24 during the pulling or tugging motions of such positioning.

After the tube 10 has been properly positioned within the duodenum 42 or jejunum 44, the endoscopist releases the forceps 38 from their gripping engagement of the stem portion 24. Even if that stem portion 24 is wetted by body fluids, the forceps 38 will not stick to that stem portion 24 upon release. Accordingly, the enteral feeding tube 10 will not move away from its proper position as the forceps are removed from the duodenum 42 or jejunum 44.

This embodiment describes the use of endoscopic forceps to position the enteral feeding tube. It will be apparent to those skilled in the art that the snare on an endoscope may also be used. This snare, when opened to a sufficiently large diameter, could be moved over the tip 28 and onto the stem portion 24. The snare could then be decreased to a diameter less than that of the tip 28. In this way, the snare would not slip off of the attachment 22 during movement of the tube 10 into its proper location within the duodenum or jejunum. After the tube 10 was properly positioned, the snare's diameter could again be increased, permitting the endoscopist to move the snare over the tip 28 of and away from the attachment 22.

Accordingly, it may be seen that the attachment 22 of the present invention, and particularly its relatively rigid but flexible stem portion 24, facilitates entry of the enteral feeding tube 10 through yet another tube in an ostomy, such as a cannula 32 or a PEG tube. In particular, the present invention avoids the "doubling-over" of prior art sutures which effectively increases the outer diameter of the feeding tube 10. The present invention also ensures proper placement of the enteral feeding tube 10 within the body of a patient 30 by providing a stem portion 24 that is made of a material which will, even when wetted with body fluids, readily release away from the forceps 38 which position that tube 10. The present invention provides all of these advantages while still maintaining a relatively low risk of puncturing organs as the feeding tube 10 is moved through the body.

While the invention has been described with reference to a preferred embodiment, it will be understood by those skilled in the art that various changes may be made and equivalents may be substituted for elements thereof without departing from the broader aspects of the invention. Also, it is intended that broad claims not specifying details of a particular embodiment disclosed herein as the best mode contemplated for carrying out the invention should not be limited to such details. Furthermore, while, generally, specific claimed details of the invention constitute important specific aspects of the invention in appropriate instances even the specific claims involved should be construed in light of the doctrine of equivalents.

What we claim is:

1. In combination, an improved enteral feeding tube having a distal and a proximal end, said feeding tube defining a feeding passageway opening to the exterior thereof adjacent its distal end of the tube through a lateral discharge opening, and an attachment secured to and forming an extension of the distal end of said feeding tube beyond said lateral opening, said attachment comprising:

a. a generally rigid stem portion of a thickness smaller than the general thickness of the feeding tube and extending from said distal end of said enteral tube in a direction generally parallel to said feeding tube, said stem portion being sufficiently rigid that it maintains its straight shape when it extends upwardly and is sufficiently flexible so as not to harm tissue when moved within the body of a patient, and so that forceps may bend the stem portion during manipulation within the patient's body; and b. an enlarged non-soluble tip at the outer end of said rigid stem portion, said tip having outer dimensions greater than the outer dimensions of the stem portion, said stem portion having a length in excess of the thickness of said tip so that it can be readily grasped by a device which pulls the feeding tube and extension thereof into a desired position within a patient's body without the grasping portion of the device occluding the lateral passageway opening at the distal end of said tube.

2. The combination of claim 1 wherein said attachment is made of a flexible polyurethane.

3. The combination of claim 1 wherein said attachment is adhered to said distal end of said enteral feeding tube.

4. The combination of claim 1 wherein said attachment is integrally molded to said distal end of said enteral feeding tube.

5. In combination, an improved enteral feeding tube having a distal and a proximal end, said feeding tube defining a feeding passageway opening laterally to the exterior thereof adjacent its distal end of the tube through a lateral discharge opening and having an extension at said distal end of said feeding tube beyond said lateral opening, said extension comprising:

a. a generally rigid stem portion of a thickness smaller than the thickness of the feeding tube and extending from said distal end of said enteral tube in a direction generally parallel to said feeding tube, said stem portion being sufficiently rigid that it maintains its straight shape when it extends upwardly and is sufficiently flexible so as not to harm tissue when moved within the body of a patient, and so that forceps may bend the stem portion during manipulation within the patient's body; and b. a spherical, non-soluble tip at one end of said rigid stem portion, said stem portion having a length in excess of the diameter of said spherical tip so that it can be readily grasped by a device which pulls the feeding tube and attachment into a desired position within a patient's body without the grasping portion of the device occluding the lateral passageway opening at the distal end of said tube.

6. An attachment for the distal end of an enteral feeding tube, said attachment comprising:

a. a generally rigid stem portion having one end adapted to be attached to the distal end of an enteral tube which has a lateral discharge opening adjacent its distal end and so as to extend in a direction generally parallel to said tube when connected to the distal end thereof, said stem portion being sufficiently rigid that it maintains its straight shape when it extends upwardly and is sufficiently flexible so as not to harm tissue when moved within the body of a patient, and so that forceps may bend the stem portion during manipulation within the patient's body; and b. a spherical, non-soluble tip at the other end of said rigid stem portion of a greater diameter than said stem portion so as to minimize the possibility that a clamping device will slip off the end of the extension, said stem portion having a length in excess of the diameter of said tip so that it can be readily grasped by a device which pulls the feeding tube and attachment into a desired position within a patient's body without the grasping portion of the device occluding the lateral opening at the distal end of said tube.

7. The attachment of claim 6 wherein said attachment is made of a flexible polyurethane.

8. The attachment of claim 6 combined with said enteral feeding tube and wherein said attachment is adhered to said distal end of said enteral feeding tube.

9. The attachment of claim 6 wherein said attachment is made of a flexible polyurethane.

10. The attachment of claim 6 wherein said attachment is adhered to said distal end of said enteral feeding tube.

11. The attachment of claim 6 wherein said enlarged tip forms an abrupt abutment so as to minimize the possibility that a clamping device will slip off the end of the attachment.

12. The combination or attachment of claim 1, 5 or 6 wherein said attachment has a socket-forming portion to receive and be connected to the end of the distal end of the enteral feeding tube.

13. In combination, an improved enteral feeding tube for placement within the gastrointestinal tract by an endoscope, said feeding tube having a distal and a proximal end and defining a feeding passageway opening laterally to the exterior thereof, and an attachment secured to and forming an extension at the distal end of said feeding tube, said attachment comprising:

a. a generally rigid stem portion of a thickness smaller than the general thickness of the feeding tube and extending from said distal end of said enteral tube in a direction generally parallel to said feeding tube, said stem portion being sufficiently rigid that it maintains its straight shape when it extends upwardly and is sufficiently flexible so as not to harm tissue when moved within the body of a patient, and so that forceps may bend the stem portion during manipulation within the patient's body; and b. an enlarged non-soluble tip at one end of said rigid stem portion, said tip having a thickness greater than the thickness of the stem portion, said stem portion having a length in excess of the thickness of said tip so that it can be readily grasped by a device which pulls the feeding tube and attachment into a desired position within a patient's body without the grasping portion of the device occluding the lateral passageway opening at the distal end of said tube.

14. The combination of claim 13 wherein said enlarged non-soluble tip is generally spherical.

15. An enteral feeding tube having a distal and a proximal end, said feeding tube defining a feeding passageway opening laterally to the exterior thereof through a lateral opening adjacent to its distal end, and said distal end having an extension beyond said lateral opening, said extension comprising:

a. a generally rigid stem portion of a thickness smaller than the thickness of the feeding tube and of a length at least several times its thickness so that it can be readily grasped by a device which pulls the feeding tube and attachment into a desired position within a patient's body, said stem portion being sufficiently rigid that it maintains its straight shape when it extends upwardly and is sufficiently flexible so as not to harm tissue when moved within the body of a patient, and so that forceps may bend the stem portion during manipulation within the patient's body; and b. an enlarged non-soluble tip at one end of said rigid stem portion.

16. The combination of claim 1, 5 or 15 wherein said enlarged tip forms an abrupt abutment so as to minimize the possibility that a clamping device will slip off the end of the attachment.

* * * * *